(12) United States Patent
Khamis et al.

(10) Patent No.: US 10,470,861 B2
(45) Date of Patent: Nov. 12, 2019

(54) ELONGATE IMPLANT SYSTEM AND METHOD FOR TREATING PELVIC CONDITIONS

(75) Inventors: Chaouki A. Khamis, Edina, MN (US); James A. Alexander, Excelsior, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 539 days.

(21) Appl. No.: 13/520,138

(22) PCT Filed: Dec. 29, 2010

(86) PCT No.: PCT/US2010/062342
§ 371 (c)(1),
(2), (4) Date: Jun. 29, 2012

(87) PCT Pub. No.: WO2011/082220
PCT Pub. Date: Jul. 7, 2011

(65) Prior Publication Data
US 2012/0283511 A1  Nov. 8, 2012

Related U.S. Application Data (60) Provisional application No. 61/291,031, filed on Dec. 30, 2009.

(51) Int. Cl.
*A61F 2/00* (2006.01)
*A61F 2/02* (2006.01)

(52) U.S. Cl.
CPC .......... *A61F 2/0036* (2013.01); *A61F 2/0004* (2013.01); *A61F 2/02* (2013.01)

(58) Field of Classification Search
CPC .... A61F 2/0095; A61F 2/0031; A61F 2/0004; A61B 2017/00805; A61B 2017/00898
See application file for complete search history.

(56) References Cited

U.S. PATENT DOCUMENTS

| 2,738,790 A | 3/1956 | Todt et al. |
| 3,124,136 A | 3/1964 | Usher |

(Continued)

FOREIGN PATENT DOCUMENTS

| AU | 2002241673 | 11/2005 |
| CA | 2404459 | 8/2005 |

(Continued)

OTHER PUBLICATIONS

Mage, PH., "L-interposition d'un treillis synthetique dans la cure par voie vaginate des prolapses genitaux," Technique chirurgicale, J. Gynecol. Obstet. Reprod. 1999:28:825-829.

(Continued)

*Primary Examiner* — Christine H Matthews
*Assistant Examiner* — Joshua Daryl D Lannu
(74) *Attorney, Agent, or Firm* — Brake Hughes Bellermann LLP (57) ABSTRACT

Implant systems can include one or more needles, such as those used in pelvic floor repair procedures, and one or more elongate implants. A syringe or similar style hollow needle can be used to deliver the elongate mesh or other implant devices through one or more small stab incisions into the target tissue location inside the pelvis, proximate the vagina. The implant devices can be placed upon insertion through the incisions to engage and pull or tighten support tissue, such as the endopelvic fascia, pubocervical fascia, rectovaginal fascia, levator muscles, or other supportive muscles or tissue within the pelvis of the patient.

4 Claims, 5 Drawing Sheets

(56) References Cited

U.S. PATENT DOCUMENTS

| | | |
|---|---|---|
| 3,311,110 A | 3/1967 | Singerman et al. |
| 3,580,313 A | 5/1971 | McKnight |
| 3,763,860 A | 10/1973 | Clarke |
| 3,858,783 A | 1/1975 | Kapitanov et al. |
| 3,924,633 A | 12/1975 | Cook et al. |
| 3,995,619 A | 12/1976 | Glatzer |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,865,031 A | 9/1989 | O'Keeffe |
| 4,873,976 A | 10/1989 | Schreiber |
| 4,932,962 A | 6/1990 | Yoon et al. |
| 4,969,892 A | 11/1990 | Burton et al. |
| 5,013,316 A | 5/1991 | Goble et al. |
| 5,053,043 A | 10/1991 | Gottesman et al. |
| 5,085,661 A | 2/1992 | Moss |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,269,783 A | 12/1993 | Sander |
| 5,281,237 A | 1/1994 | Gimpelson |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,571,139 A | 11/1996 | Jenkins, Jr. |
| 5,591,206 A | 1/1997 | Moufarrege |
| 5,628,756 A | 5/1997 | Barker, Jr. et al. |
| 5,643,320 A | 7/1997 | Lower et al. |
| 5,669,935 A | 9/1997 | Rosenman et al. |
| 5,683,349 A | 11/1997 | Makower et al. |
| 5,709,708 A | 1/1998 | Thal |
| 5,725,541 A | 3/1998 | Anspach, III et al. |
| 5,741,282 A | 4/1998 | Anspach, III et al. |
| 5,807,403 A | 9/1998 | Beyar et al. |
| 5,842,478 A | 12/1998 | Benderev et al. |
| 5,919,232 A | 7/1999 | Chaffringeon et al. |
| 5,922,026 A | 7/1999 | Chin |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,027,523 A | 2/2000 | Schmieding |
| 6,036,701 A | 3/2000 | Rosenman |
| 6,042,583 A | 3/2000 | Thompson et al. |
| 6,048,351 A | 4/2000 | Gordon et al. |
| 6,071,290 A | 6/2000 | Compton |
| 6,074,341 A | 6/2000 | Anderson et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,241,736 B1 | 6/2001 | Sater et al. |
| 6,328,744 B1 | 12/2001 | Harari et al. |
| 6,387,041 B1 | 5/2002 | Harari et al. |
| 6,406,480 B1 | 6/2002 | Beyar et al. |
| 6,414,179 B1 | 7/2002 | Banville |
| 6,482,214 B1 | 11/2002 | Sidor, Jr. et al. |
| 6,494,906 B1 | 12/2002 | Owens |
| 6,506,190 B1 | 1/2003 | Walshe |
| 6,575,897 B1 | 6/2003 | Ory et al. |
| 6,592,515 B2 | 7/2003 | Thierfelder |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin et al. |
| 6,638,284 B1 | 10/2003 | Rousseau et al. |
| 6,648,921 B2 | 11/2003 | Anderson |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,884,212 B2 | 4/2005 | Thierfelder et al. |
| 6,908,473 B2 | 6/2005 | Skiba et al. |
| 6,911,003 B2 | 6/2005 | Anderson et al. |
| 6,936,052 B2 | 8/2005 | Gellman et al. |
| 6,953,428 B2 | 10/2005 | Gellman et al. |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,558 B2 | 7/2006 | Gellman et al. |
| 7,083,637 B1 | 8/2006 | Tannhauser |
| 7,087,065 B2 | 8/2006 | Ulmsten et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,299,803 B2 | 11/2007 | Kovac |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Anderson et al. |
| 7,410,460 B2 | 8/2008 | Benderev |
| 7,413,540 B2 | 8/2008 | Gellman et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,637,860 B2 | 12/2009 | MacLean |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,766,926 B2 | 8/2010 | Bosely et al. |
| 7,942,898 B2* | 5/2011 | Ewers .............. A61B 17/00234 606/222 |
| 7,981,024 B2 | 7/2011 | Levy |
| 8,172,745 B2 | 5/2012 | Rosenblatt |
| 2002/0007222 A1 | 1/2002 | Desai |

(56) References Cited

U.S. PATENT DOCUMENTS

| | | |
|---|---|---|
| 2002/0028980 A1 | 3/2002 | Thierfelder et al. |
| 2002/0058959 A1* | 5/2002 | Gellman ............... 606/185 |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0010929 A1 | 1/2003 | Prieve et al. |
| 2003/0050530 A1* | 3/2003 | Neisz et al. ............. 600/29 |
| 2003/0065402 A1 | 4/2003 | Anderson et al. |
| 2003/0176875 A1 | 9/2003 | Anderson |
| 2003/0220538 A1* | 11/2003 | Jacquetin ........... A61F 2/0045 600/37 |
| 2004/0015057 A1 | 1/2004 | Rocheleau et al. |
| 2004/0030262 A1* | 2/2004 | Fisher ............. A61L 24/0015 600/564 |
| 2004/0064014 A1* | 4/2004 | Melvin ............. A61F 2/2481 600/37 |
| 2004/0073235 A1 | 4/2004 | Lund |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0096751 A1* | 5/2005 | Gerber ............. A61B 17/00234 623/23.66 |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0229596 A1 | 10/2006 | Weiser et al. |
| 2006/0257446 A1* | 11/2006 | Tropsha ............. A61B 17/12 424/423 |
| 2007/0015953 A1 | 1/2007 | MacLean |
| 2007/0173864 A1 | 7/2007 | Chu |
| 2008/0039678 A1 | 2/2008 | Montpetit et al. |
| 2008/0045782 A1 | 2/2008 | Jimenez et al. |
| 2008/0140218 A1 | 6/2008 | Staskin et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |
| 2010/0022822 A1 | 1/2010 | Walshe |
| 2010/0056857 A1* | 3/2010 | Nordmeyer ............... 600/30 |
| 2010/0179575 A1 | 7/2010 | Von Pechmann et al. |
| 2010/0261950 A1 | 10/2010 | Lund |
| 2010/0280627 A1 | 11/2010 | Hanes, II |
| 2011/0124954 A1 | 5/2011 | Ogdahl et al. |
| 2011/0174313 A1 | 7/2011 | Von Pechmann et al. |
| 2012/0016185 A1 | 1/2012 | Sherts et al. |

FOREIGN PATENT DOCUMENTS

| | | |
|---|---|---|
| CA | 2404459 C | 8/2005 |
| CN | 101534746 A | 9/2009 |
| DE | 2305815 | 2/1973 |
| DE | 4220283 C2 | 5/1994 |
| DE | 19544162 | 4/1997 |
| EP | 0632999 A1 | 1/1995 |
| EP | 1060714 A3 | 9/2002 |
| FR | 2852813 A1 | 1/2004 |
| FR | 2861580 A1 | 5/2005 |
| IT | 1299162 | 4/1998 |
| JP | 2009515564 A | 4/2009 |
| JP | 2009527272 A | 7/2009 |
| KR | 20090021367 A | 3/2009 |
| SU | 1225547 A1 | 4/1986 |
| SU | 1342486 A | 10/1987 |
| SU | 1342486 A1 | 10/1987 |
| WO | WO9317635 A1 | 9/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9835606 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO1999/059477 | 11/1999 |
| WO | WO9959477 A1 | 11/1999 |
| WO | WO0064370 A1 | 2/2000 |
| WO | WO0013601 A1 | 3/2000 |
| WO | WO0040158 A2 | 7/2000 |
| WO | WO0057812 A1 | 10/2000 |
| WO | WO0074633 A2 | 12/2000 |
| WO | WO0106951 A1 | 2/2001 |
| WO | WO106951 A1 | 2/2001 |
| WO | WO0139670 A1 | 6/2001 |
| WO | WO0156499 A1 | 8/2001 |
| WO | WO0234124 A2 | 5/2002 |
| WO | WO02071953 A2 | 9/2002 |
| WO | WO02078552 A1 | 10/2002 |
| WO | WO2078552 A1 | 10/2002 |
| WO | WO03017848 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03068107 A1 | 8/2003 |
| WO | WO03092546 A2 | 11/2003 |
| WO | WO03096929 A1 | 11/2003 |
| WO | WO2004012626 A1 | 2/2004 |
| WO | WO2005079702 A1 | 9/2005 |
| WO | WO2005122954 A1 | 12/2005 |
| WO | WO2006108145 A1 | 10/2006 |
| WO | WO2007011341 A1 | 1/2007 |
| WO | WO2007016083 A1 | 2/2007 |
| WO | WO 2007016698 A2 * | 2/2007 |
| WO | WO2007027592 A2 | 3/2007 |
| WO | WO2007081955 A1 | 7/2007 |
| WO | 2007097994 A2 | 8/2007 |
| WO | WO2007/097994 | 8/2007 |
| WO | WO2007097994 | 8/2007 |
| WO | WO2007146784 A2 | 12/2007 |
| WO | WO2007149348 A2 | 12/2007 |
| WO | 2008013867 A1 | 1/2008 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

Petros, P.E., "Vault Prolapse II: restoration of dynamic vaginal supports by infracoccygeal sacropexy, and axial day-case vaginal procedure," Int. Urogynecol. J. (2001) 12:296-303.

Petros, et al., "The posterior fornix syndrome: a multiple symptom complex of pelvic pain and abnormal urinary symptoms deriving from laxity in the posterior fornix of vagina," Scand. J. Urol. Nephrol. Suppl. No. 153, pp. 89-95 (1993).

Richter, Kurt, "Massive eversion of the vagina: pathogenesis, diagnosis, and therapy of the 'true' prolapse of the vaginal stump," Clinical Obstet. & Gyne., vol. 25, No. 4, pp. 897-911 (1982).

Sanz et al., "Modification of abdominal sacrocolpopexy using a suture anchor system," Journal of Reproductive Medicine, vol. 48, No. 7, pp. 496-501 (2003).

(56) References Cited

OTHER PUBLICATIONS

Subak et al., "Cost of pelvic organ prolapse surgery in the United States," Am. College Obstet. & Gyne., vol. 98, No. 4, pp. 464-452 (2001).
Sullivan et al., "Total pelvic mesh repair," Dis Colon Rectum, vol. 44, No. 6 pp. 857-864 (2001).
Swift et al., "Case-control study of etiologic factors in the development of severe pelvic organ prolapse," Int. Urogynecol. J. 12:187-192 (2001).
Visco et al., "Vaginal mesh erosion after abdominal sacral colpopexy," Am. J. Obstet. Gynecol. vol. 184, No. 3, pp. 297-303 (2001).
Weber et al., "Anterior vaginal prolapse review of anatomy and techniques or surgical repair," Obstet. & Gyne., vol. 89, No. 2, pp. 310-318 (1997).
Winters et al., "Abdominal sacral colpopexy and abdominals enterocele repair in the management of vaginal vault prolapse," Urology 56 (Suppl. 6A) pp. 56-64(2000).
English Translation of Office Action from Japanese Patent Office, Related JP Patent Application No. 2012-547263, dated Jun. 24, 2014.
International Preliminary Report on Patentability, PCT/US2010/062342, Related PCT Application, dated Jul. 4, 2012.
International Search report, PCT/US2010/062342, Related PCT Application, dated Mar. 11, 2011.
Written Opinion of International Searching Authority, PCT/US2010/062342, Related PCT Application, dated Mar. 11, 2011.
First Office Action for Japanese Application No. 2016-030914, dated Jan. 25, 2017, 8 pages.
Mouly, et al., "Vaginal Reconstruction of a Complete Vaginal Prolapse: The Trans Obturator Repair", Journal of Urology, vol. 169, Apr. 2003, p. 183.
Amundsen et al., "Anatomical correction of vaginal vault prolapse by uterosacral ligament fixation in women who also require a pubovaginal sling," The J. Of Urology, vol. 169, 1770-1776, May 2003.
Cervigni et al., "The use of synthetics in the treatment of pelvic organ prolapse," Current Opinion in Urology 2011, 11:429-435.
Eglin et al., Transobturator subvesical mesh: tolerance and short-term results of a 103 case continuous series, Service de gynecologic clinque Dhampeau 32 (Nov. 2002).
Farnsworth, B. N., "Posterior intravaginal slingplasty (infracoccygeal sacropexy) for severe posthysterectomy and vaginal vault prolapse—a preliminary report on efficacy and safety," Int. Urogynecol J (2002) 13:4-8.
Heit et al., "Predicting treatment choice for patients with pelvic organ prolapse," The Am. College of Obstet. & Gyn., vol. 101, No. 6, Jun. 2003.
Julian, Thomas, "The efficacy of Marlex mesh in the repair of severe, recurrent vaginal prolapse of the anterior midvaginal wall," Am. J. Obstet. Gynecol. vol. 175, No. 6, pp. 1471-1476 (1996).
Karram et al., "Surgical Treatment of Vaginal Vault Prolapse," Urogynecology and reconstructive pelvic surgery, Mosby (1999).
Luber, et al., "The demographics of pelvic floor disorders: current observations and future projections," Am. J. Obstet. Gynecol. vol. 184, No. 7, pp. 1496-1504 (2001).
Mage, PH., "L-interposition d'un treillis synthetique dans la cure par voie vaginale des prolapses genitaux," Technique chirurgicale, J. Gynecol. Obstet. Reprod. 1999:28:825-829.
Marchionni, et al., "True incidence of vaginal vault prolapse: thirteen years of experience," J. of Reproductive Medicine, vol. 44, No. 8, pp. 679-685 (1999).
Migliari et al., "Tension-free vaginal mesh repair for anterior vaginal wall prolapse," Eur. Urol. 2000;38:151-155.
Morley et al., "Sacrospinous ligament fixation for eversion of the vagina," Am. J. Obstet. Gynecol., vol. 158, No. 4, pp. 871-881 (1988).
Morley, Patrick, "Vaginal reconstruction of a complete vaginal prolapse: the transobturator repair," Journal of Urology, vol. 169 (4) supplement, p. 183 (2003).
Nicita, Giulio, "A new operation for genitourinary prolapse," The Journal of Urology, vol. 160, 741-745 (1998).
Paraiso, et al., "Laparoscopic surgery for enterocele, vaginal apex prolapse and rectocele," Int. Urogynecol. J. 10:223-239 (1990).
Paraiso, et al., "Pelvic support defects and visceral and sexual function in women treated with sacrospinous ligament suspension and pelvic reconstruction," Am. J. Obstet. & Gyne. vol. 175, No. 6 (1996).
Extended European Search Report for European Application No. 10841672.8, dated Jan. 2, 2018, 8 pages.
First Examination Report for Indian Application No. 5742/CHENP/2012, dated Feb. 22, 2019, 5 pages.

\* cited by examiner

ELONGATE IMPLANT SYSTEM AND METHOD FOR TREATING PELVIC CONDITIONS

PRIORITY

This Application claims priority to and the benefit of U.S. Provisional Application No. 61/291,031, filed on Dec. 30, 2009, which is hereby incorporated herein by reference in its entirety.

FIELD OF THE INVENTION

The present invention relates generally to surgical methods and apparatus and, more specifically, to minimally invasive prolapse repair via needles, and methods for forming and using the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Fecal incontinence, like urinary incontinence, has proven to be challenging to treat. Patients whose fecal incontinence is caused by external anal sphincter injury is treated surgically, as with a sphincteroplasty. Other patients are considered to have neurogenic or idiopathic fecal incontinence and efforts to treat these patients have been less successful. Various procedures, such as postanal repair, total pelvic floor repair, muscle transposition techniques, dynamic gracioplasty, artificial sphincter procedures, and sacral nerve stimulation. Success has been limited, and the various treatment modalities can result in morbidity.

There is a desire to obtain a minimally invasive yet highly effective repair devices and methods that can be used to treat incontinence (urinary or fecal), and/or organ prolapse and other pelvic conditions.

SUMMARY OF THE INVENTION

The present invention describes systems, needles and methods for treating pelvic conditions such as incontinence, vaginal prolapse (including various forms such as enterocele, cystocele, rectocele, apical or vault prolapse, uterine descent, etc.), and other pelvic conditions caused by muscle and ligament weakness.

Embodiments of the systems can include one or more needles, such as those used in pelvic floor repair procedures. A syringe or similar style hollow needle can be used to deliver elongate mesh or other implant devices through one or more small stab incisions into the target tissue location inside the pelvis. The implant devices can be placed upon insertion through the incisions to engage and pull or tighten support tissue, e.g., endopelvic fascia, pubocervical fascia, rectovaginal fascia, levator muscles, or other supportive muscles or tissue within the pelvis of the patient. The devices can include one or more mesh members, rods, or braided members adapted to support the respective target tissue or organs.

The implant devices can engage, pull or otherwise tension tissue to cause the tissue to tighten and provide slack reduction for improved support. As such, embodiments of the implants can be utilized to eliminate the need for mesh or other supportive structures under the urethra that is common with incontinence slings.

The present invention can include surgical instruments, implantable articles, and methods for urological applications, particularly for the treatment of stress and/or urge urinary incontinence, fecal incontinence, and prolapse and perineal floor repairs. As noted, the usual treatments for incontinence include placing a sling to either compress the urethral sphincter or to elevate or support the neck of the bladder defects.

DETAILED DESCRIPTION OF PREFERRED EMBODIMENTS

Referring generally to FIGS. 1-12, various embodiments of pelvic repair systems 10 are disclosed. One aspect of the present invention is an apparatus and method of treating urinary incontinence in males or females. In various embodiments, one or more implants or implant members are placed in strategically located positions to pull up or otherwise tighten tissue and/or muscle lateral to the urethra, or anterior or posterior to the vagina, to generally re-establish the original anatomical structure of the patient.

Structures or portions of the various embodiments detailed herein can be constructed of materials such as polypropylene, polyglycolide, poly-1-lactides, or other known biodegradable (re-absorbable) or non-biodegradable polymers. Further, growth factors or stem cells can be seeded or otherwise provided with one or more of the components of the devices to facilitate healing or tissue in-growth. In addition to introduction and deployment of the devices or components with a needle introducer device, a cannula or catheter system can be utilized as well.

Figure 1:
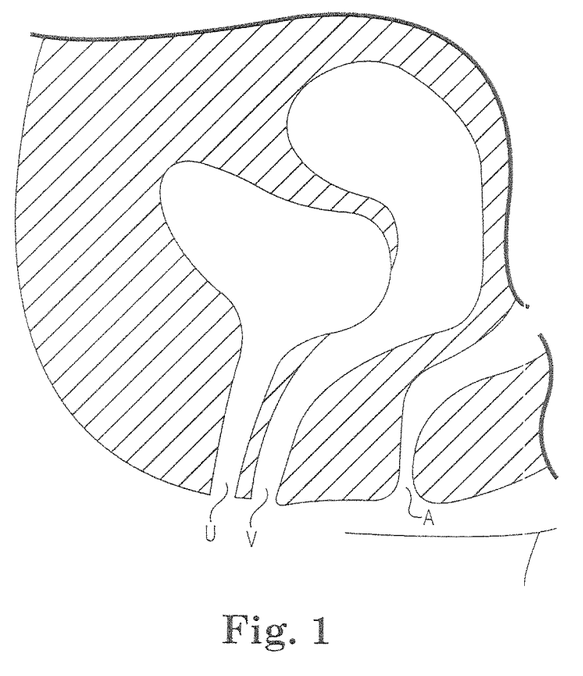
FIG. 1 shows a cross-sectional schematic view of various relevant structures of the female anatomy in accordance with implantation of the present invention.

FIG. 1 shows the general anatomical structure of the female anatomy, including the Urethra U, Vagina V, and Anus A.

Figure 2:
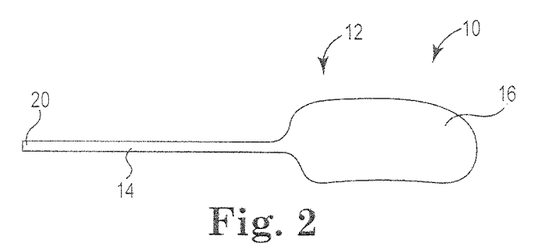
FIG. 2 shows a delivery tool in accordance with embodiments of the present invention.

The systems 10 can include one or more syringe or needle devices 12, as shown in FIG. 2. The needle devices 12 can include a hollow needle portion 14 and a handle portion 16. The need portion 14 can include an internal lumen adapted to receive, deploy and release one or more implants 18. The hollow needle portion 14 can include a distal tip 20 adapted to create and traverse one or more small stab incisions proximate (e.g., anterior or posterior) the Vagina V. The needle portion 14 can be straight, curved or helical. Further, the device 12 can include one or more actuation or trigger mechanisms adapted to selectively retain or deploy one or more implants 18 from the device 12 (e.g., needle lumen).

The distal tip 20 and at least a portion of the needle portion 14 are adapted for insertion to create and traversal into the stab incisions into the target tissue location inside the pelvis of the patient. The various systems 10, implants, tools, features and methods detailed herein are envisioned for use with or can utilize all or part of the known implant and repair systems (e.g., for male and female), features and methods, including those disclosed in U.S. Pat. Nos. 7,267,645, 7,500,945, 7,229,453, 7,407,480, 7,393,320, 7,351,197, 7,347,812, 7,303,525, 7,291,104, 7,025,063, 6,691,711, 6,648,921, 6,612,977, 6,592,515, and International Patent Publication Nos. WO 2010/027796, WO 2008/057261 and WO 2007/097994, and U.S. Patent Publication Nos. 2002/151762 and 2002/147382. Accordingly, the above-identified disclosures and publications are fully incorporated herein by reference in their entirety.

Figure 3:
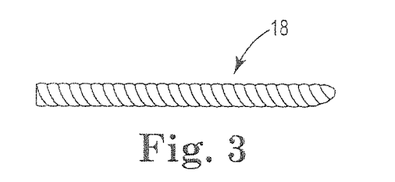
FIGS. 3-6 show exemplary elongate implants in accordance with embodiments of the present invention.
Figure 4:
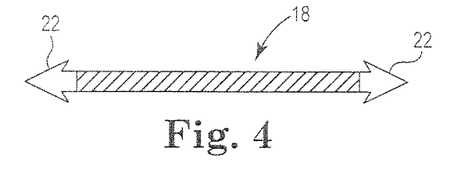
Figure 5:
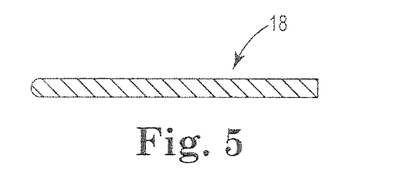
Figure 6:
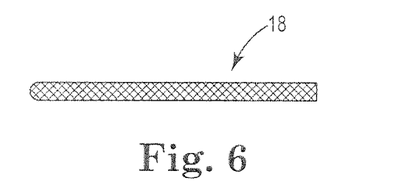

FIGS. 3-6 show various exemplary embodiments of the implants 18. Generally, the implants are constructed in an elongate or rod-shaped construct. The implants 18 can be shaped, constructed or formed as elongate mesh strips (FIG. 6), elongate rods (FIG. 5), or braided rods (FIG. 3). Further, various embodiments of the implants 18 can include one or more end anchors 22 to facilitate tissue engagement and retention during deployment and positioning. In addition, portions of the implants 18 can include extending members, protrusions, barbs, tines, surface roughness, surface edges or like features to facilitate tissue fixation of the implant 18 upon deployment.

Figure 7:
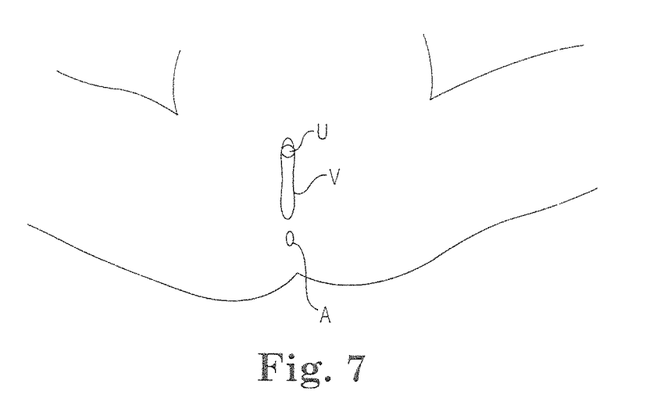
FIG. 7 shows a female patient and relevant anatomical structure.
Figure 8:
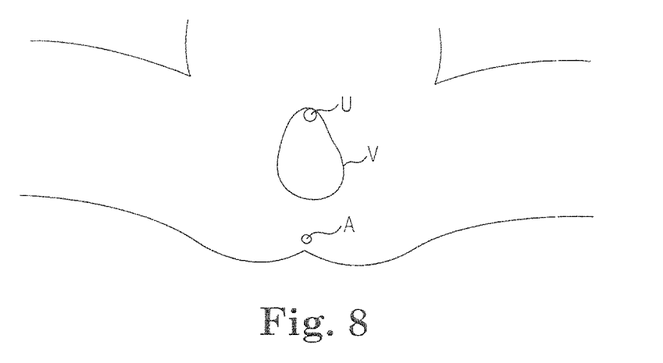
FIG. 8 shows a female patient with an expanded vagina in preparation for implantation in accordance with embodiments of the present invention.

As shown in FIGS. 7-12, various available steps or procedures for the pelvic repair system 10 are depicted. First, the patient is placed in the supine position, as shown in FIG. 7. The vagina V is then expanded, as demonstrated in FIG. 8. Various known tools, retractors, balloons or like devices and procedures can be utilized to achieve this vaginal expansion.

One or more of the needle devices 12 are provided for external penetration or stab incisions proximate or along the periphery of the vagina V. Alternatively, the stab incisions can be first made by the physician with a surgical tool and then the needle devices 12 can be introduced to deploy the needle 14 and implants 18 through the one or more stab incisions.

Next, the needle device 12 can be inserted through the one or more incisions to deploy the implant 18 (e.g., mesh, rod, braided material, or a like implant) into and from the inner lumen of the needle 14. Then, while holding the implant 18 in place, the hollow tube needle 14 is extracted to leave the implant 18 in place for pelvic floor support. A number of these steps can be repeated until the desired number of needles or implants are deployed, or the desired support is achieved. The configurations of the present invention provide a system adapted to control the depth of the implant to provide consistency and optimal placement. Further, the distal tip 20 or needle 14, and the implant 18, are adapted to penetrate target tissue or anatomical structure within the pelvis, around the vagina V to provide the desired engagement and tissue support to address the incontinence or prolapse weaknesses.

Figure 9:
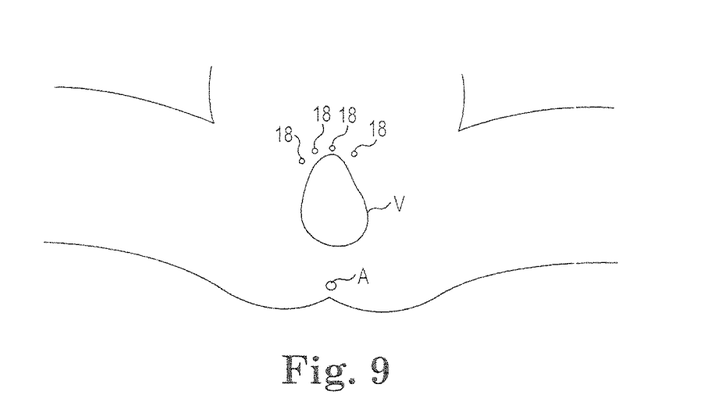
FIGS. 9-11 show implantation of elongate implants within stab incisions in accordance with embodiments of the present invention.
Figure 10:
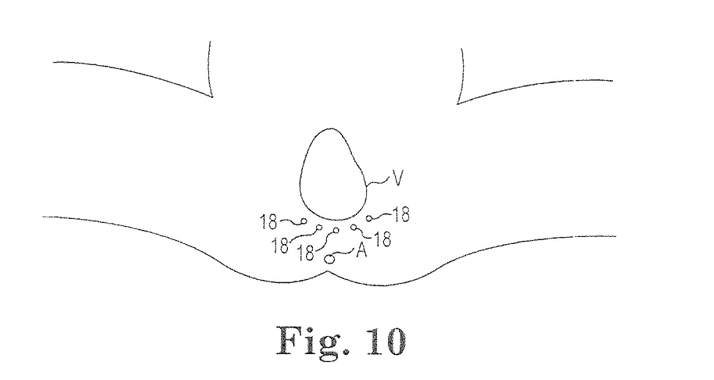
Figure 11:
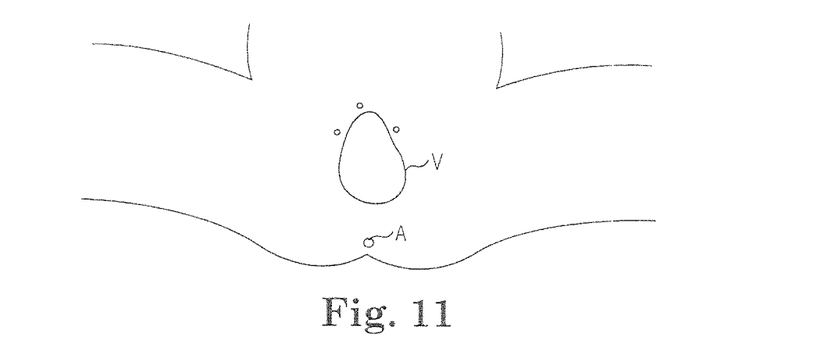
Figure 12:
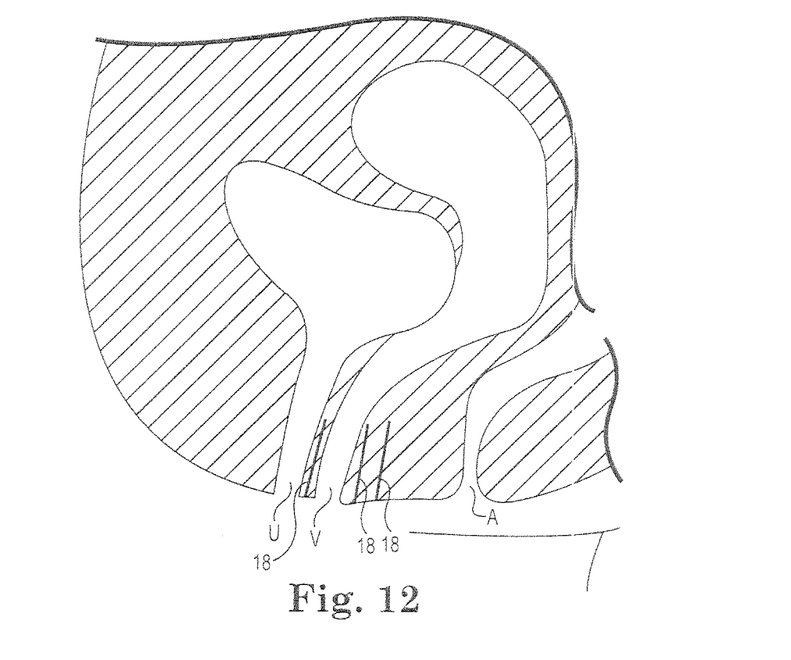
FIG. 12 shows a cross-section schematic view of various relevant anatomical structures and deployed elongate implants in accordance with embodiments of the present invention.

In certain embodiments, the needle 14 is adapted for insertion through the stab incisions such that the implants 18 can be inserted into or otherwise engaged with internal support tissue around the vagina, urethra and the like, e.g., pubocervical fascia, rectovaginal fascia, endopelvic fascia, levator muscles, just to name a few. As shown in FIGS. 9-11, the spacing, placement and pattern for deploying implants 18 can vary greatly. Various anterior patterned (relative to vagina) and positioned implants 18 are shown in FIGS. 9 and 11. FIG. 10 shows an exemplary posterior pattern and positioning for the implants 18. The quantity, positioning and incision points for the implants 18 shown in the figures are merely for demonstrative purposes and a myriad of other patterns and implant numbers are envisioned for the present invention. FIG. 12 demonstrates various exemplary implants 18 deployed and engaged within the patient to provide the desired support and tensioning of the present invention. The implants 18 can extend into the pelvic region or target engagement tissue a full length of the relative organ or lumen (e.g., urethra U or vagina V), or along a distance short of the entire organ or lumen length.

Embodiments of the present invention provide key advantages over conventional methods and systems, including controlled implant depth to reduce implant variation, reduced risk of extrusion or erosion, reduced recovery time because of the lack of large incisions, blunt dissections, sutures, and the like. Various portions of the systems 10 can be constructed of known or compatible polymer or metal materials (e.g., Nitinol).

Alternative embodiments of the present invention can be used to restore levator ani structures to provide further support. Use of the system to restore or support other anatomical structures are envisioned as well. Further, guided catheter tools or systems, magnetically guided sensors and tools, and other known devices and delivery systems can be employed with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A method of treating a pelvic disorder in a patient, comprising:
providing a delivery tool having a handle and a needle, the needle being coupled to the handle, the needle including an internal lumen, the needle including a distal portion, the distal portion having a distal tip for creating external stab incisions;

providing a plurality of elongate rod implants including a first elongate rod implant, a second elongate rod implant, and a third elongate rod implant;

making a plurality of external stab incisions in a patient, proximate a vagina, with the needle of the delivery tool, the plurality of external stab incisions including a first external stab incision at a first location, a second external stab incision at a second location, and a third external stab incision at a third location, the first location, the second location, and the third location being at different locations;

providing the first elongate rod implant within the internal lumen of the needle of the delivery tool;

inserting the distal portion of the needle within the first external stab incision;

deploying the first elongate rod implant from the internal lumen such that the first elongate rod implant extends linearly with respect to the vagina of the patient;

providing the second elongate rod implant within the internal lumen of the needle;

inserting the distal portion of the needle within the second external stab incision;

deploying the second elongate rod implant from the internal lumen of the needle such that the second elongate rod implant extends linearly within a pelvic region, adjacent and proximate the first elongate rod implant, providing the third elongate rod implant within the internal lumen of the needle;

inserting the distal portion of the needle within the third external stab incision; and deploying the third elongate rod implant from the internal lumen of the needle such that the third elongate rod implant extends linearly within the pelvic region.

2. The method of claim 1, wherein making the plurality of external stab incisions includes making the plurality of external stab incisions anterior to the vagina.

3. The method of claim 1, wherein making the plurality of external stab incisions includes making the plurality of external stab incisions posterior to the vagina.

4. The method of claim 1, wherein the first elongate rod implant includes a first end portion and a second end portion, and the first elongate rod implant includes a first tissue anchor coupled to the first end portion, and a second tissue anchor coupled to the second end portion.

* * * * *